(12) United States Patent
Bevilacqua et al.

(10) Patent No.: US 6,958,815 B2
(45) Date of Patent: Oct. 25, 2005

(54) METHOD AND APPARATUS FOR PERFORMING QUANTITATIVE ANALYSIS AND IMAGING SURFACES AND SUBSURFACES OF TURBID MEDIA USING SPATIALLY STRUCTURED ILLUMINATION

(75) Inventors: Frederic Bevilacqua, Costa Mesa, CA (US); David Cuccia, Irvine, CA (US); Anthony J. Durkin, Costa Mesa, CA (US); Bruce J. Tromberg, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 310 days.

(21) Appl. No.: 10/391,166

(22) Filed: Mar. 18, 2003

(65) Prior Publication Data

US 2003/0184757 A1 Oct. 2, 2003

Related U.S. Application Data

(60) Provisional application No. 60/365,578, filed on Mar. 19, 2002.

(51) Int. Cl.[7] .............................................. G01N 21/55
(52) U.S. Cl. ..................................................... 356/445
(58) Field of Search ................................ 356/445, 446, 356/603, 604

(56) References Cited

U.S. PATENT DOCUMENTS 5,625,458 A * 4/1997 Alfano et al. ................ 356/446
5,640,247 A * 6/1997 Tsuchiya et al. ............. 356/446

* cited by examiner

*Primary Examiner*—F. L. Evans
(74) *Attorney, Agent, or Firm*—Daniel L. Dawes; Myers Dawes Andras & Sherman LLP

(57) ABSTRACT

Illumination with a pattern of light allows for subsurface imaging of a turbid medium or tissue, and for the determination of the optical properties over a large area. Both the average and the spatial variation of the optical properties can be noninvasively determined. Contact with the sample or scanning is not required but may be desired. Subsurface imaging is performed by filtering the spectrum of the illumination in the Fourier domain but other filtering approaches, such as wavelet transform, principle component filter, etc may be viable as well. The depth sensitivity is optimized by changing the spatial frequency of illumination. A quantitative analysis of the average optical properties and the spatial variation of the optical properties is obtained. The optical properties, i.e. reduced scattering and absorption coefficients are determined from the modulated transfer function, MTF.

32 Claims, 5 Drawing Sheets

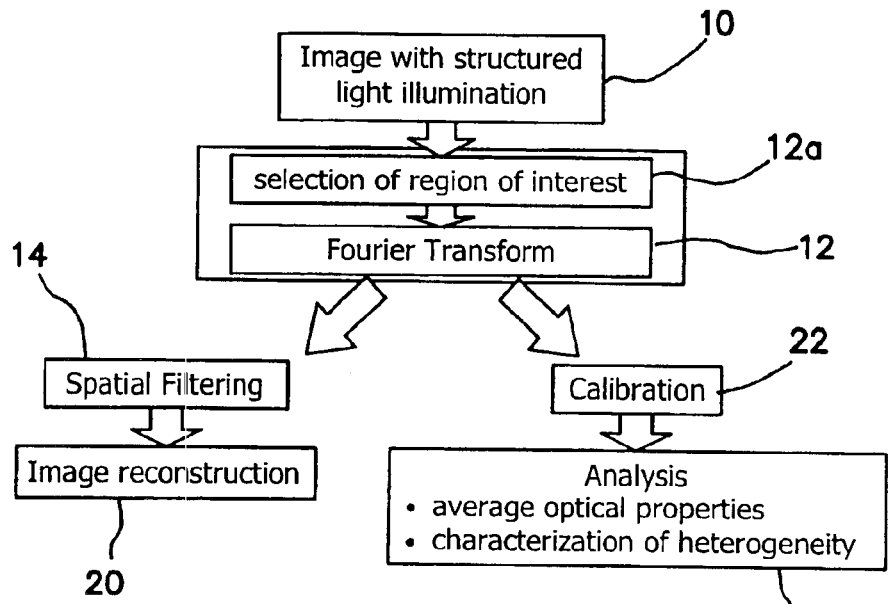
FIG. 1
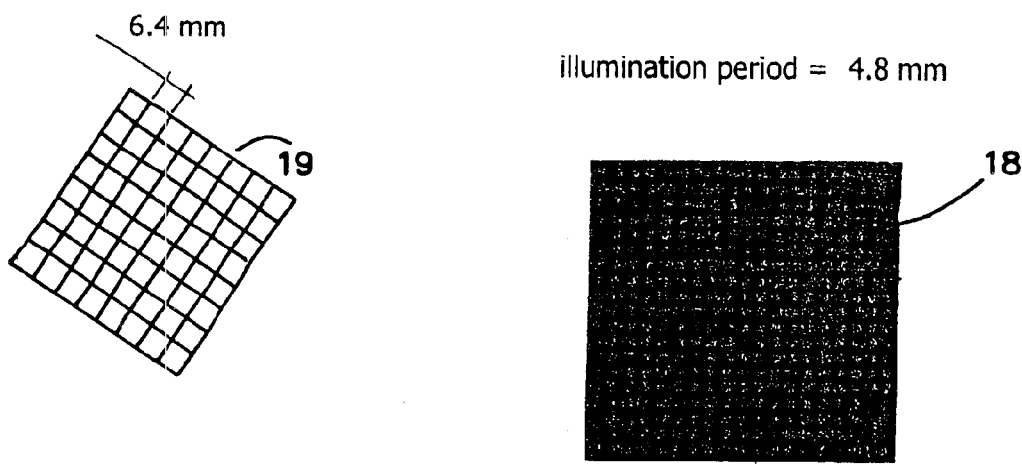
FIG. 2A
FIG. 2B

METHOD AND APPARATUS FOR PERFORMING QUANTITATIVE ANALYSIS AND IMAGING SURFACES AND SUBSURFACES OF TURBID MEDIA USING SPATIALLY STRUCTURED ILLUMINATION

RELATED APPLICATIONS

The present application is related to U.S. Provisional Patent Application Ser. No. 60/365,578, filed Mar. 19, 2002, which is incorporated herein by reference and to which priority is claimed pursuant to 35 USC 119.

GOVERNMENT RIGHTS

This invention was made with Government support under Grant No. RR001192, awarded by the National Institutes of Health. The Government has rights in this invention.

BACKGROUND OF THE INVENTION

1. Field of the Invention

The present invention relates to optical measurement of turbid media and in particular to optical measurement tissue absorption and scattering parameters and tissue imaging. The invention may also be used as a means to monitor a chemical process, for example, a pharmaceutical slurry.

2. Description of the Prior Art

Reflectance spectroscopy is a technique for characterizing turbid media that has become widely used in medical diagnostics. In many cases access to quantitative information, for example, chromophore concentrations is desired. In the strictest sense, this may require the ability to separate the effects of absorption from those of scattering. However, it may be that calibrated, structured reflectance data may be sufficiently quantitative without going to the step of separating scattering from absorption. Fundamentally, the coefficient of absorption $\mu_a$ and the coefficient of reduced scattering $\mu_s'$ can be determined by a series of reflectance measurements performed in one of three domains, namely, time (with a fast pulse of light), frequency (with a sinusoidally modulated source of light), and steady state (with a source of constant intensity but multiple detectors at different distances).

Unsurprisingly, these three techniques have different merits and limitations. Spatially resolved steady-state techniques are relatively inexpensive and are more readily suited for the determination of $\mu_a$ and $\mu_s'$ over large, continuous ranges of wavelengths than are the other methods. However, the steady-state approach works best when measurements are performed with a combination of short (~1 transport mean free path) and long (many transport mean free paths) source-detector separations. Ideally, the optical properties of the sample should not vary over the ranges of volumes probed by the various measurements. The larger the spread of distances probed, the more likely that heterogeneities, such as those found in biological tissue, will distort the data from the predictions of the model. One approach to limiting this effect, given that the shortest separations provide great stability for the calculation of $\mu_s'$, is to use relatively short (<10 mm) source-detector separations. Inasmuch as the mean probing depth scales with the source-detector separation, with this approach such measurements are sensitive to superficial components (to depths of less than 5 mm for typical biological tissues).

Time-domain and frequency-domain techniques are well suited for deeper (>1 cm for biological tissue) investigations. Moreover, they can be performed with only one or a few source-detector separations, which makes them more robust for use in studying heterogeneous samples. Because such techniques require sources that can be pulsed or modulated rapidly, covering a large wavelength range requires a tunable laser or an extensive collection of laser diodes, both of which can be expensive, difficult to maintain, and slow to cover the entire spectrum. This is an important drawback, because the quantification of chromophore concentrations can be significantly affected by use of a limited number of wavelengths.

Thus, a means has been devised to use steady-state and frequency-domain reflectance measurements in tandem to obtain broad wavelength coverage with increased penetration depth. This method comprises performing frequency-domain photon migration measurements on a turbid medium sample. It also includes performing steady-state reflectance measurements on the same turbid medium sample. It further includes combining the results of the frequency-domain photon migration measurements with the results of the steady-state reflectance measurements for obtaining a unique spectrum for the turbid medium sample.

Light photons from a plurality of different laser diode light sources are emitted into human body tissue from a predetermined delivery point on the surface of a human body. In this method light photons are emitted from a white light source into the same human body tissue from the same predetermined delivery point on the surface of the human body. The method then includes collecting the light photons received at a spaced collection point on the surface of the human body after such light photons have traveled through the human body tissue intermediate the delivery and collection points. The predetermined characteristics of the light photons from the different light sources are then collected to provide an indication of the composition of the traversed human body tissue. The prior methodology is described in detail in U.S. Provisional Patent Application Ser. No. 60/308,507 filed on Jul. 27, 2001, entitled "Broadband Absorption Spectroscopy in Turbid Media By Combined Frequency-Domain and Steady-State Methods and Apparatus", assigned to the same assignee as the present invention and is incorporated herein by reference.

Absorption and scattering properties provide unique insight into tissue function and structure. "Optical biopsy" techniques have been developed based on the quantitative measurements of such properties and have shown promising results in clinical trials. Nevertheless, most of these techniques as described above reply on "point spectroscopy" and measure only a single, small area of tissue at a time. Such investigations would greatly benefit from imaging capabilities and/or being performed over a larger region of interest. Scanning or multiplexing can be used to overcome such a disadvantage, but is typically slow and cumbersome to implement.

What is needed is some kind of methodology and apparatus whereby larger a real information or data relating to the absorption and scattering properties of tissue or turbid media may be rapidly acquired in a single measurement.

BRIEF SUMMARY OF THE INVENTION

The invention uses a patterned light exposure on a sample for subsurface imaging of turbid media such as tissue. A determination of the optical properties of the sample can then be determined in a single measurement over a large area. Both the average and the spatial variation of the optical properties, such as the absorption and scattering coefficients, can be determined. Contact with the sample or scanning is not required. But in certain embodiments, contact may be desired and the method could still be employed.

Typically, a square grid of dots or lines, of various spatial frequencies, is used as the patterned illumination. The transformation of the illumination pattern, which is a consequence of the sample composition, contains the optical property information, which can be deduced according to previously known analytical algorithms. For example, sample composition, can also be deduced, based on capturing data in the structure illumination geometry, using methods based on multivariate calibration approach. It is also possible to recover optical properties from frequency domain phase measurement (FDPM) data using a chemometric approach which is amendable to modulated imaging. Two types of analysis can be applied and they are not mutually exclusive. According to the invention both types of analysis can be performed separately or together. Subsurface imaging can be performed by filtering the spatial pattern of the illumination in the Fourier domain. Analysis in Fourier space is one possibility, but it is expressly contemplated as being within the scope of the invention that wavelet based filtering, filtering using principle components, other mathematical spaces can be equivalently substituted. The average depth probed by the patterned illumination differs from uniform illumination. The depth sensitivity, which is a function of the details of the sample composition, can be optimized by changing the spatial frequency of illumination. Moreover, the combination of several of images performed with various spatial frequencies can allow for the reconstruction of the three dimensional volume of the sample.

A quantitative analysis of the average optical properties and the spatial variation of the optical properties can be achieved. The optical properties, i.e. reduced scattering and absorption coefficients are determined from the modulated transfer function, MTF, by conventional means well known in the art. If the sample is nonhomogenous, an average, direction dependent MTF will result from the application of the method, which allows for the determination of the optical properties as a function of direction.

More particularly, the invention is defined as a method for simultaneously imaging surface and subsurface of turbid media and determining quantitative average optical properties over a variable area of interest of the sample, with a single measurement or combining several measurements.

The capability of the method of the invention is demonstrated in the case where only few measurements are taken, for example by taking three slightly different patterns, which is still significantly more efficient compared to a scanning system requiring thousands of measurements. The invention is not restricted a the single measurement method.

The method comprises the steps of exposing the sample to a periodic pattern of illumination; and receiving the data image from the sample. The data image of the sample is mathematically transformed using one or more image processing algorithms, such spatial filtering, deconvolution techniques, Fourier transform, Wavelet transform, and principle component filtering.

In one embodiment the transformed data image of the sample is then spatially filtered and the filtered transformed data image of the sample is reconstructed.

In the illustrated embodiment the step of exposing the sample to a periodic pattern of illumination comprises exposing the sample to a periodic pattern of illumination dots. The periodic pattern of dots is characterized by a periodic distance between the dots. In such a case the step of exposing the sample to a periodic pattern comprises probing the sample to a depth of approximately one half the dot spacing.

More generally the periodic pattern is characterized by a periodic distance and where exposing the sample to a periodic pattern comprises probing the sample to a depth which is a function of the periodic distance. By exposing the sample to a plurality of periodic patterns, each of which is characterized by a periodic distance, the sample is probed to a plurality of depths.

The method further comprises the step of determining a modulation transfer function of the periodic pattern of illumination. This step of determining a modulation transfer function of the periodic pattern of illumination comprises the steps of exposing a homogenous standard with a predetermined periodic pattern having a known spatial Fourier spectrum and receiving a reflectance data image from the standard. The reflectance data image of the standard is Fourier transformed and ratioed with the transformed data image of the sample to obtain a map of the modulation transfer function. A map of scattering and absorption properties is generated from the map of the modulation transfer function. It is also possible to generate averages of scattering and absorption properties of the sample from the modulation transfer function.

It is expressly contemplated by the invention that the steps of exposing the sample to a periodic pattern of illumination, receiving the data image, mathematically transforming the data image to a more convenient coordinate space, spatially filtering the transformed data image, and reconstructing the filtered transformed data image will be repeated for areas of different sizes to provide multiscale analysis of the sample.

Another embodiment of the invention is defined as a method of determining subsurface optical properties of a sample of turbid media over an area of the sample with a single measurement comprising the steps of exposing the sample to a periodic pattern of illumination; receiving the data image of the sample; exposing a homogenous standard with a periodic pattern having a known spatial Fourier spectrum; receiving a reflectance data image from the standard; Fourier transforming or more generally, mathematically transforming, the data image of the sample; Fourier transforming or more generally, mathematically transforming the reflectance data image of the standard; and ratioing the transformed data image of the sample with the reflectance data image of the standard to obtain a map of the modulation transfer function. However, in general the Fourier spectrum of the standard need not be known a priori. The data acquired from the standard need only be reproducible and amenable to transformation.

Again method further comprises the step generating a map of scattering and absorption properties from the map of the modulation transfer function or generating averages of scattering and absorption properties of the sample from the modulation transfer function. These steps of: exposing the sample and standard to a periodic pattern of illumination, receiving the data image of the sample and reflectance data image of the standard; Fourier transforming the data image of the sample and the reflectance data image of the standard, and ratioing the transformed data image of the sample with the reflectance data image of the standard to obtain a map of the modulation transfer function can be repeated for areas of different sizes to provide multiscale analysis of the sample.

It should also be expressly understood that the invention includes an apparatus for performing the above methods, which includes a source of patterned illumination, a camera for receiving the data image from the sample and standard, and a computer or processing circuit for performing the data processing functions. The source, camera, and processing circuit include not only the examples disclosed in the illustrated embodiment below, but any devices for performing the recited functions which devices are now known or later devised. According to the concept and scope of the invention all such devices are deemed equivalent by virtue of performing the recited function regardless of the manner or way in which the function might be specifically performed.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

BRIEF DESCRIPTION OF THE DRAWINGS

FIG. 1 is a simplified block diagram whereby the methodology of the invention is illustrated.

FIGS. 2a–2e are graphic depictions of the input patterned light and the resulting data and modulated transfer function, MTF. FIG. 2a is a plan view of a mesh which is embedded in an Intralipid phantom. FIG. 2b is a plan view of the acquired data image. FIG. 2c is a sequence of images depicting the masking step in the Fourier domain. FIG. 2d is the resulting reconstructed image of the phantom according to the invention. FIG. 2e is the computed corresponding average modulated transfer function, MTF.

Figure 2C:
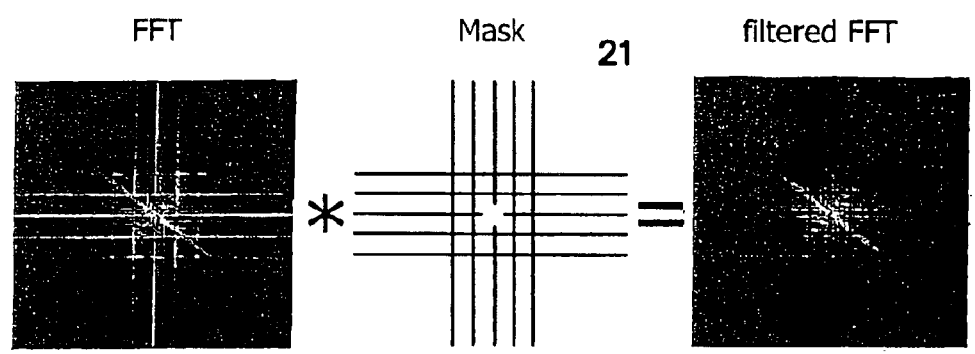

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

Illumination with patterned or structured light, such as described below in connection with FIG. 2b, allows for subsurface imaging of turbid media such as tissue and allows for the determination of the optical properties over a large area. Both the average and the spatial variation of the optical properties can be determined. The invention provides a fast, non-contact, scan-free method to image and quantify the optical properties of a tissue. In general, the method does not have to be a non-contacting methodology, although to be able to perform the method in a non-contact mode is a significantly enhanced benefit and utility.

The method is based on spatially structured or patterned illumination, and can be thought of as a generalization of spatially-resolved optical measurements with a single source. Moreover, structured or patterned illumination has the advantage of providing for integration of subsurface imaging, quantitative determination of scattering and absorption properties, and surface profiling in a single measurement. In most embodiments, for example, in order to quantify optical properties, one has to acquire reference data from a calibration standard in addition to acquiring data from the sample of interest. This requirement should not be considered to be at odds with the statement that the invention can be executed "in a single measurement", since reference data in a broad sense can be considered not to be measured data, but calibration data. Furthermore, such an illumination scheme potentially accommodates the use of multiple wavelengths simultaneously. Thus, although the illustrated embodiment is described as being conducted at a single wavelength, it is to be expressly understood that multiple wavelengths or wavelength bands may be employed in a manner consistent with the teachings of the invention.

As shown in the block diagram of FIG. 1 the method begins at step 10 with tissue being illuminated with spatially structured or patterned light such as shown in FIG. 2b. Typically, a square grid of dots or lines, of various spatial frequencies, is used. It is to be understood that any pattern now known or later devised may be used, and that the scope of the invention is not limited to the illustrated pattern nor for that matter even to a geometric pattern, but contemplates free-form patterns. The transformation of the illumination pattern, due to the turbidity the sample or tissue contains the optical property information. In other words, the periodic pattern of illumination penetrates the tissue, is scattered back to a CCD camera and the image data is then processed according to the invention.

Since the illumination in the illustrated embodiment is periodic, the analysis is better performed in the spatial Fourier domain at step 12 in FIG. 1. Two types of analysis can be applied. First, subsurface imaging can be performed by filtering the spectrum of the illumination in the Fourier domain at step 14. The Fourier domain image is reconstructed at step 20 and is graphically depicted in the example of FIGS. 2a–2d in FIG. 2c discussed below. The average depth probed by the structured or patterned illumination differs from uniform illumination. Furthermore, the depth sensitivity can be optimized by changing the spatial frequency of illumination. The depth which is probed is approximately of the order of one half the periodicity or distance between dots 16 in pattern 18 of FIG. 2b. This depth selectivity results from the fact that small source-to-detector separations are more sensitive to superficial tissue than large source-to-detector separations. The effective sensitivity to depth, as a function of the spatial frequency of the illumination, is assessed using Monte Carlo simulations. Thus, it is to be further understood that a plurality of illumination patterns 18 may be projected onto the sample in order to obtain a series of variable depth, large area data collections from the tissue.

Second, a quantitative analysis of the average optical properties and the spatial variation of the optical properties can be achieved. If the sample is homogeneous, the two-dimensional Fourier transform of the image is the spectrum of the illumination multiplied by the modulation transfer function (MTF) of the tissue, which is defined as a Fourier transform of the spatially-resolved reflectance of a point illumination. The MTF can be directly determined after a proper calibration of the system as implemented in step 22 where a known standard is illuminated and its average and spatial properties compared to the measured properties in step 24. Any optical standard may be used, such as a uniform slab of titanium dioxide or an Intralipid sample, or a known test patterned sample of the same.

Figure 3:
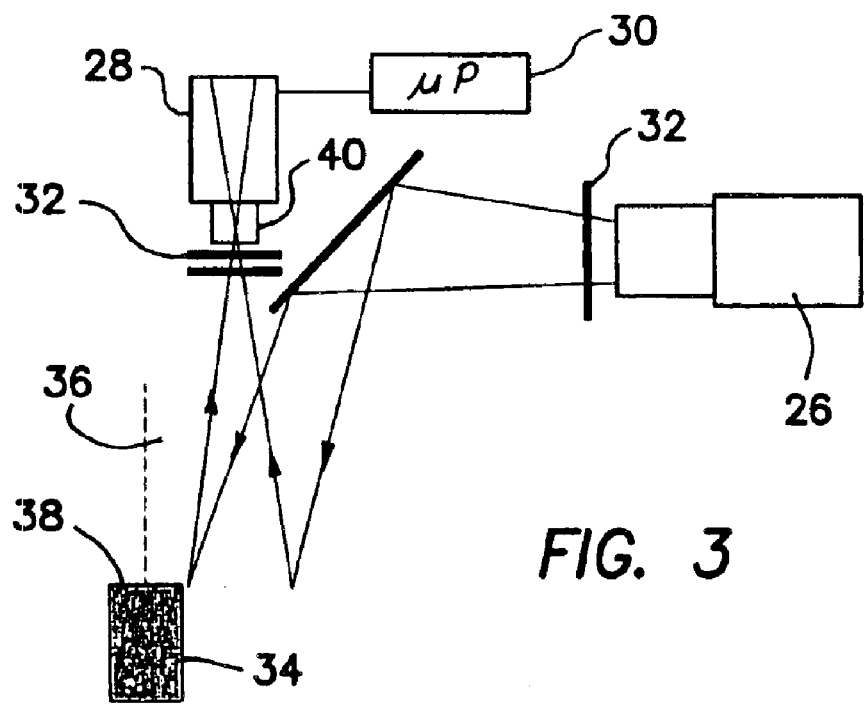
FIG. 3 is a simplified diagram of an apparatus for obtaining the images according to the invention.

Preliminary data have been acquired using a slide projector 26 in FIG. 3 to provide the illumination pattern 18 and CCD camera 28 coupled to computer 30 to take the image data. Various illumination patterns 18, e.g. dots, lines, etc, are projected onto the tissue or sample 34 as shown in FIG. 3 and are captured by Peltier-cooled 16 bit CCD camera 28. Again it is to be understood that the means for creating the illumination patterns 18 and the means for capturing the data can assume a large number of equivalent devices without departing from the teachings of the invention. Any device now known or later devised for creating a light pattern, and any device now known or later devised for recording the reflection of the same from a sample can be equivalently employed.

As diagrammatically shown in FIG. 3 specular reflection is carefully avoided by illuminating the sample at a small angle to the normal direction 36 of the surface 38 of the sample 34. Linear polarizers 32 are also used to avoid specular reflection and to reduce the sensitivity to the very top surface 38 of the sample or tissue 36. Interference filters 40 are used to select a narrow band wavelength, e.g. $\lambda=670$ nm in the illustrated embodiment, $\Delta\lambda=20$ nm at full width half maximum. Reflectance standards are used to calibrate the measured intensity, and to correct for spatial nonuniformity in both the illumination and imaging system.

Figure 4A:
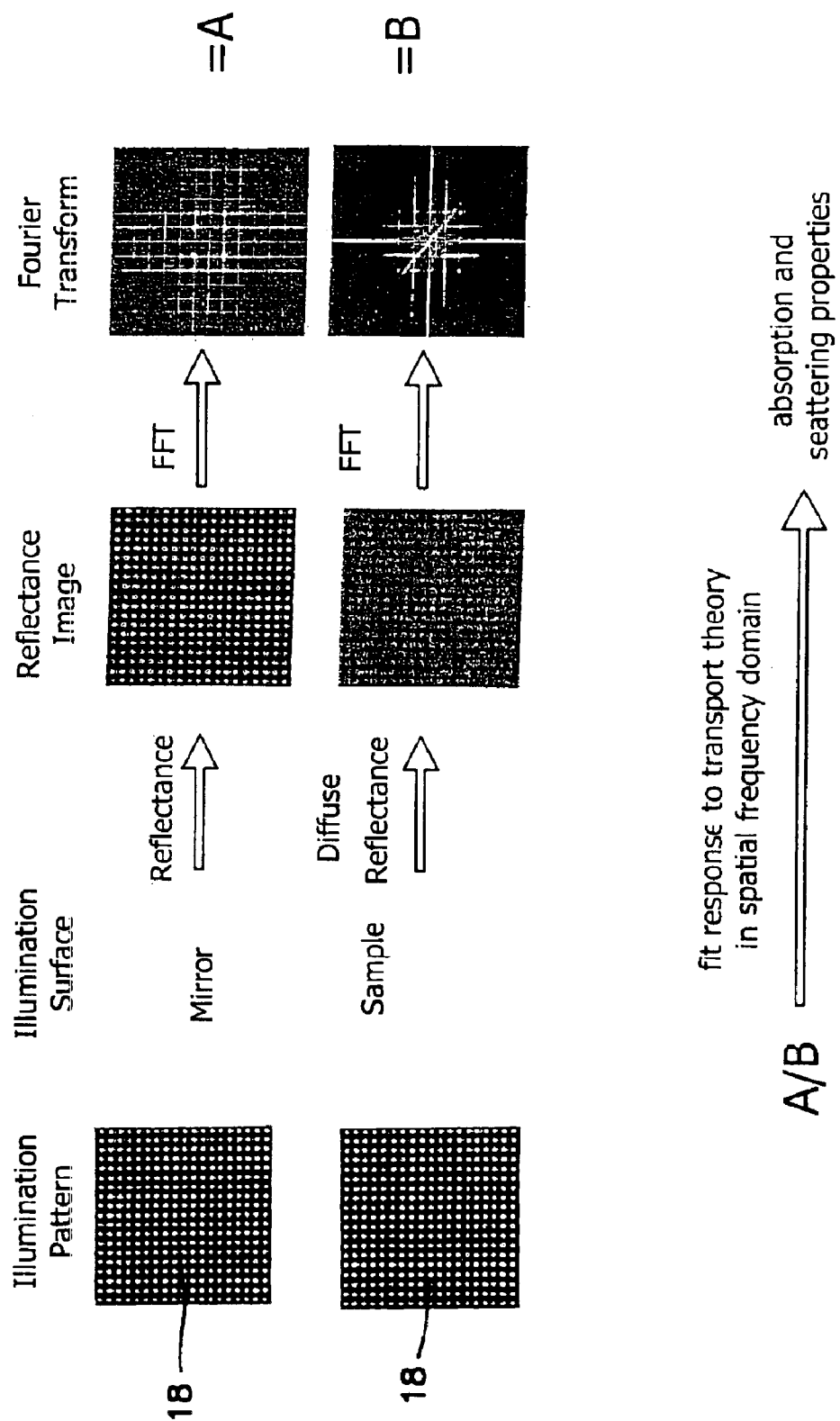
FIG. 4a is a diagram depicting the principal steps to obtain the direction dependent absorption and reduced scattering coefficients.
Figure 4B:
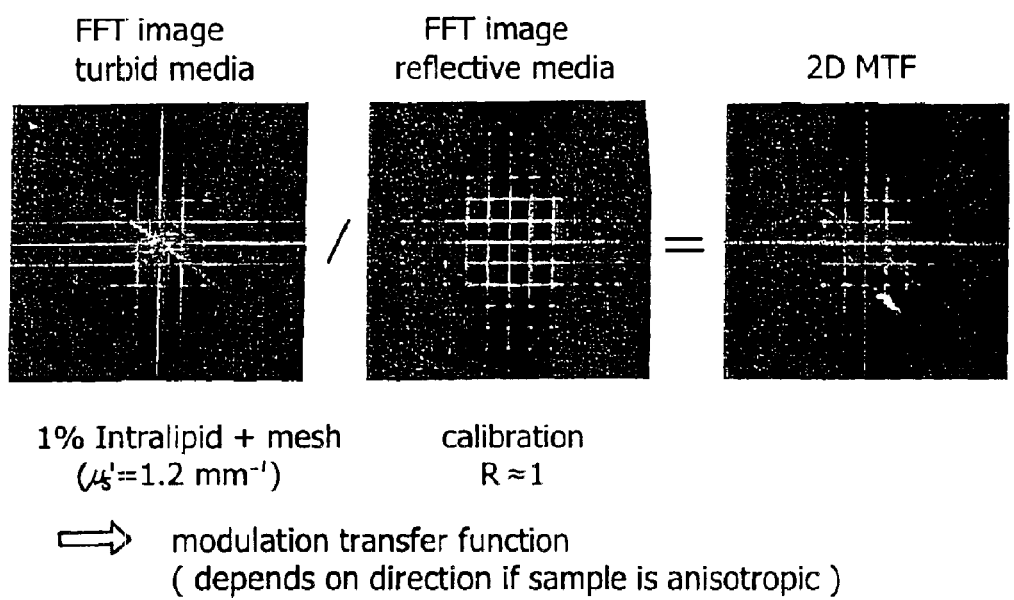
FIG. 4b is a diagram depicting the process whereby a calibrated, quantified image of the two dimensional modulated transfer function is obtained according to the invention.

FIG. 4 diagrammatically depicts the process wherein identical illumination patterns in tracks A and B are projected onto the surface of a highly reflective standard used as the target or sample (not shown) in track A and onto a tissue surface used as the target or sample in track B. Specular and diffuse reflection results respectively from the mirror and tissue samples and distinct reflectance images are obtained. Fourier transforms applied to both reflectance images result in corresponding Fourier reflectance data images. The image of track A and B are ratioed pixel by pixel to obtain a two dimensional, calibrated map in the Fourier domain. The ratioed map is then fit using conventional transport theory to result in a directional or two dimensional map of the scattering and absorption properties.

Figure 2D:
Figure 2E:
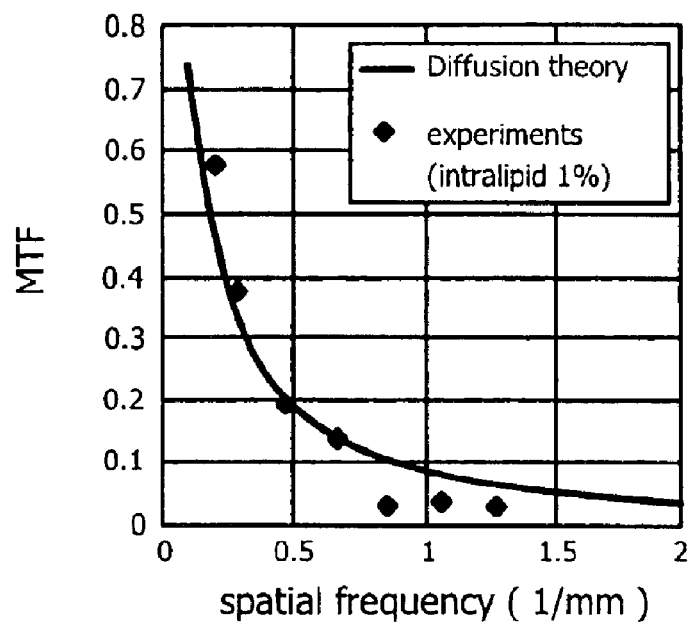

In the illustrated embodiment of FIGS. 2a–2d phantoms 34 made of Intralipid solution were used in the illustrated embodiment. Various heterogeneities such as absorbing spheres or meshes are submerged, or introduced into the phantom. FIG. 2a shows an absorbing mesh 19 which was placed 1 mm below the surface in a 1% Intralipid sample 34 ($\mu'=1.2$ mm$^{-1}$). The absorbing mesh 19 was rotated with respect to the light source pattern by approximately 45° as shown in FIG. 2a. The acquired image is showed in FIG. 2b. The illumination pattern can be seen as overlaid the acquired image in FIG. 2b. After filtering the illumination by applying a subtraction exposure mask 21 in the Fourier domain to remove the incident pattern of illumination as shown in the sequence of drawings of FIG. 2c, the image of the mesh is reconstructed as depicted in FIG. 2d. In FIG. 2c the Fourier domain image is shown in the left side, mask 21 in the center and the resulting filtered Fourier domain image in the right side of FIG. 2c. In parallel to this image reconstruction, the average modulation transfer function, MTF, as a function of spatial frequency is also computed after calibration as also shown in FIG. 2e. A fit to the diffusion solution or Monte Carlo simulation enables one to determine the optical properties according to well understood conventional principles from the graph of FIG. 2e.

Thus, it may now be appreciated that a method for subsurface, quantitative analysis of tissue optical properties has been described based on spatially modulated light. This method can be applied with no contact to the tissue over a large area and could be used in a variety of diagnostic studies that require wide-field tissue characterization.

The optical properties, i.e. reduced scattering and absorption coefficients can be determined from the MTF by conventional means well known in the art as depicted in FIG. 4a. If the sample is nonhomogenous, an average, direction dependent MTF can be defined which allows for the determination of the optical properties as a function of direction. Such cases have been found to be relevant in skin for example. As in the case with the process in FIG. 4, a Fourier domain image of a sample can be obtained as shown in the left hand side of FIG. 4a. This two dimensional Fourier domain image is ratioed with a calibration reflectance Fourier domain image from a mirror or reflectance standard to then obtain a computed two-dimensional Fourier domain image of the modulated transfer function, MTF, as shown in the right hand side of FIG. 4a.

Moreover, the characteristics of both the average and spatial variation of the optical properties can be characterized, which may be useful for the tracking alterations in tissue that arise during the dysplasia-carcinoma sequence or other disease states. The medical diagnostic application and use of the invention is not limited to surface application or dermatology, but is generally applicable. For example, it is expressly contemplated that the invention may be employed as the detecting element in arthroscopic devices used for both therapeutic and diagnostic procedures, including surgical procedures or biopsies.

Finally, it must be noted that the two-dimensional Fourier transform of the image can be applied either on the full image or on arbitrarily smaller subregions. In this manner spatial variations in the optical properties can be analytically derived from a single data measurement down to the point where even a single point of sensible data comprises the entire subregion. The analysis can therefore be performed at several scaling factors, from a localized region to a large area (but with different precision on the analysis of the optical properties). Note that such multi-scale analysis could also be performed by a wavelet transform.

Further, while the invention has been described in terms of the optical properties of the sample, but it may also be used to measure or map the fluorescence of a sample arising from fluorophores. The apparatus and method of the invention can be used to recover optical properties, in addition to a depth sensitive "image" of fluorophores. A depth sensitive "image" of fluorophore distribution can then be produced in addition to optical properties and fluorophore concentration of the sample.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. A method of determining surface or subsurface optical properties of a sample of turbid media over an area of the sample with a single measurement comprising:
    exposing the sample to a periodic pattern of illumination;
    receiving the data image from the sample;
    selecting a region of interest of the sample;
    transforming the data image of the selected region of interest of the sample;
    spatially filtering the transformed data image of the selected region of interest of the sample; and
    reconstructing the filtered transformed data image of the selected region of interest of the sample.

2. The method of claim 1 where exposing the sample to a periodic pattern of illumination comprises exposing the sample to a periodic pattern of illumination dots.

3. The method of claim 2 where the periodic pattern of dots is characterized by a periodic distance between the dots and where exposing the sample to a periodic pattern comprises probing the sample to a depth of approximately one half the dot spacing at the sample surface.

4. The method of claim 1 where the periodic pattern is characterized by a periodic distance and where exposing the sample to a periodic pattern comprises probing the sample to a depth which is a function of the periodic distance.

5. The method of claim 4 further comprising exposing the sample to a plurality of periodic patterns, each of which is characterized by a periodic distance so that exposing the sample to a plurality of periodic patterns comprises probing the sample to a plurality of depths.

6. The method of claim 1 further comprising determining a modulation transfer function of the periodic pattern of illumination.

7. The method of claim 6 where determining a modulation transfer function of the turbid sample for the periodic pattern of illumination comprises:
    exposing a homogenous standard with a predetermined periodic pattern having a known measurable and reproducible spatial Fourier spectrum;
    receiving a reflectance data image from the standard;
    selecting a region of interest of the sample;
    transforming the reflectance data image of the standard;
    ratioing the transformed data image of the selected region of the sample with the reflectance data image of the standard to obtain a map of the modulation transfer function;
    generating a map of scattering and absorption properties from the map of the modulation transfer function; and
    generating averages of scattering and absorption properties of the sample from the modulation transfer function.

8. The method of claim 1 where exposing the sample to a periodic pattern of illumination, receiving the data image, Fourier transforming the data image, spatially filtering the transformed data image, and reconstructing the filtered transformed data image is repeated for various regions of interest to provide a map of the optical properties.

9. The method of claim 1 where exposing the sample to a periodic pattern of illumination, receiving the data image, Fourier transforming the data image, spatially filtering the transformed data image, and reconstructing the filtered transformed data image is repeated for areas of different sizes to provide multiscale analysis of the sample.

10. The method of claim 9 where providing multiscale analysis is provided post-processing without retaking the data image.

11. A method of determining surface or subsurface optical properties of a sample of turbid media over an area of the sample with a single measurement comprising:
    exposing the sample to a periodic pattern of illumination;
    receiving the data image of the sample;
    exposing a homogenous standard with a predetermined periodic pattern having a known spatial Fourier spectrum;
    receiving a reflectance data image from the standard;
    selecting a region of interest of the sample;
    Fourier transforming the data image of the selected region of interest of the sample;
    selecting a region of interest of the standard;
    Fourier transforming the reflectance data image of the selected region of interest of the standard; and
    ratioing the transformed data image of the sample with the reflectance data image of the standard to obtain a map of the modulation transfer function.

12. The method of claim 11 where exposing the sample to a periodic pattern of illumination is repeated with a sequence of different wavelengths and/or filters.

13. The method of claim 11 further comprising generating a map of scattering and absorption properties from the map of the modulation transfer function.

14. The method of claim 11 further comprising generating averages of scattering and absorption properties of the sample from the modulation transfer function.

15. The method of claim 11 where exposing the sample and standard to a periodic pattern of illumination, receiving the data image of the sample and reflectance data image of the standard; Fourier transforming the data image of the sample and the reflectance data image of the standard, and ratioing the transformed data image of the sample with the reflectance data image of the standard to obtain a map of the modulation transfer function is repeated for areas of different sizes to provide multiscale analysis of the sample.

16. An apparatus of determining subsurface optical properties of a sample of turbid media over an area of the sample with a single measurement comprising:
a source to expose the sample to a periodic pattern of illumination;
a camera to receive the data image from the sample; and
a signal processor to Fourier transform the data image of the sample, to spatially filter the transformed data image of the sample, and to reconstruct the filtered transformed data image of the sample.

17. The apparatus of claim 16 where the signal processor is a computer.

18. The apparatus of claim 16 where the signal processor is an optical spatial filter.

19. The apparatus of claim 16 where source generates a periodic pattern of illumination dots.

20. The apparatus of claim 19 where the periodic pattern of dots is characterized by a periodic distance between the dots and where the source probes the sample to a depth of approximately one half the dot spacing.

21. The apparatus of claim 16 where the periodic pattern is characterized by a periodic distance and where the source probes the sample to a depth which is a function of the periodic distance.

22. The apparatus of claim 21 where the source exposes the sample to a plurality of periodic patterns, each of which is characterized by a periodic distance so that exposing the sample to a plurality of periodic patterns comprises a source which probes the sample to a plurality of depths.

23. The apparatus of claim 16 where the signal processor deduces a modulation transfer function of the periodic pattern of illumination.

24. The apparatus of claim 23 where the source exposes a homogenous standard with a predetermined periodic pattern having a known spatial Fourier spectrum, the camera receives a reflectance data image from the standard, the signal processor Fourier transforms the reflectance data image of the standard, and ratios the transformed data image of the sample with the transformed reflectance data image of the standard to obtain a map of the modulation transfer function.

25. The apparatus of claim 24 where the signal processor generates a map of scattering and absorption properties from the map of the modulation transfer function.

26. The apparatus of claim 16 where the signal processor generates averages of scattering and absorption properties of the sample from the modulation transfer function.

27. The apparatus of claim 16 where repeated exposures of the sample by the source, repeated collection of data images by the camera, repeated Fourier transforming the data image, spatially filtering the transformed data image, and reconstructing the filtered transformed data image by the signal processor is performed for areas of different sizes to provide multiscale analysis of the sample.

28. An apparatus of determining subsurface optical properties of a sample of turbid media over an area of the sample with a single measurement comprising:
a homogenous standard with a periodic pattern having a known spatial Fourier spectrum;
a source to expose the sample and the standard to a periodic pattern of illumination;
a camera to receive the data image of the sample and a reflectance data image from the standard;
a signal processor to Fourier transform the data image of the sample, Fourier transform the reflectance data image of the standard, and ratio the transformed data image of the sample with the reflectance data image of the standard to obtain a map of the modulation transfer function.

29. The apparatus of claim 28 where the signal processor generates a map of scattering and absorption properties from the map of the modulation transfer function.

30. The apparatus of claim 28 where the signal processor generates averages of scattering and absorption properties of the sample from the modulation transfer function.

31. The apparatus of claim 28 where the source repeatedly exposes the sample and standard to a periodic pattern of illumination, the camera repeatedly receives the data image of the sample and reflectance data image of the standard; and the signal processor repeatedly Fourier transforms the data image of the sample and the reflectance data image of the standard, and repeatedly ratios the transformed data image of the sample with the reflectance data image of the standard to repeatedly obtain a map of the modulation transfer function for areas of different sizes to provide multiscale analysis of the sample.

32. The method of claim 1 further comprising repeating exposing the sample to a periodic pattern of illumination, receiving the data image from the sample, selecting a region of interest of the sample, transforming the data image of the selected region of interest of the sample, spatially filtering the transformed data image of the selected region of interest of the sample; and reconstructing the filtered transformed data image of the selected region of interest of the sample over a temporal span without changing the periodic pattern of illumination in order to track dynamic changes in the sample over time.

* * * * *